United States Patent [19]

Brunner et al.

[11] Patent Number: 4,704,464

[45] Date of Patent: Nov. 3, 1987

[54] TUMOR RETARDING (1-BENZYL-ETHYLENEDIAMINE)-PLATIN (II)-COMPLEXES

[75] Inventors: Henri Brunner, Lappersdorf; Helmut Schonenberger, Pentling; Manfred Schmidt, Gelnhausen; Ulrich Holzinger, Passau; Gerfried Unger, Frankfurt; Jurgen Engel, Alzenau, all of Fed. Rep. of Germany

[73] Assignee: ASTA-Werke Aktiengesellschaft Chemische Fabrik, Bielefeld, Fed. Rep. of Germany

[21] Appl. No.: 831,911

[22] Filed: Feb. 21, 1986

[30] Foreign Application Priority Data

Feb. 23, 1985 [DE] Fed. Rep. of Germany ....... 3506468

[51] Int. Cl.[4] ............................................. C07F 15/00
[52] U.S. Cl. ..................................... 556/137; 548/109; 548/402; 549/3; 549/206
[58] Field of Search ..................... 556/137; 549/3, 206; 548/109, 402

[56] References Cited

U.S. PATENT DOCUMENTS

| 4,234,500 | 11/1980 | Hoeschele et al. | 514/492 X |
| 4,250,189 | 2/1981 | Hydes et al. | 556/137 |
| 4,477,387 | 10/1984 | Kidani et al. | |
| 4,594,418 | 6/1986 | Speer et al. | 556/137 X |
| 4,598,091 | 7/1986 | Schonenberger et al. | 556/137 X |

FOREIGN PATENT DOCUMENTS

| 55300 | 7/1982 | European Pat. Off. . |
| 2916145 | 10/1985 | Fed. Rep. of Germany . |
| 1380228 | 1/1975 | United Kingdom . |

OTHER PUBLICATIONS

Chemical Abstracts 104 199664p (1986).

Hall et al., J. Inorganic Biochemistry 11, pp. 139–149 (1979).

*Primary Examiner*—Helen M. S. Sneed
*Attorney, Agent, or Firm*—Cushman, Darby & Cushman

[57] ABSTRACT

There are described (1-benzylethylenediamine)-platin-(II)-complexes of the general formula:

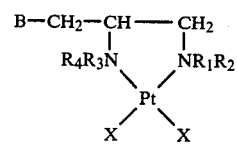

wherein the radicals $R_1$, $R_2$, $R_3$, and $R_4$ are the same or different and are hydrogen, a $C_1$–$C_6$-alkyl group, a benzyl group, or a phenylethyl group, and B is a thienyl radical, an indolyl radical, an imidazolyl radical, or a phenyl radical substituted by the radicals $R_5$, $R_6$, an $R_7$ which are the same or different and are hydrogen, halogen, trihalomethyl, $C_1$–$C_6$-alkyl, hydroxy, $C_1$–$C_6$-alkoxy, phenoxy, benzyloxy, $C_1$–$C_6$-alkanoyloxy, benzoyloxy, $C_1$–$C_6$-alkanesulfonyloxy, carboxy, $C_1$–$C_6$-carbalkoxy, cyano, aminocarboxyl, aminocarbonyl, which contains one or two $C_1$–$C_6$-alkyl radicals, $C_1$–$C_6$-alkylcarbonyl, nitro, amino, $C_1$–$C_6$-alkylamino, di-$C_1$–$C_6$-alkylamino, $(C_1$–$C_6$-alkyl$)_3$N+, $C_1$–$C_6$-alkanoylamino, $C_1$–$C_6$-alkyl-$C_1$–$C_6$-alkanoylamino, $C_1$–$C_6$-alkanesulfonylamino, $C_1$–$C_6$-alkyl-$C_1$–$C_6$-alkanesulfonylamino, aminosulfonyl, aminosulfonyl which contains one or two $C_1$–$C_6$-alkyl radicals, $C_1$–$C_6$-alkoxysulfonyl ($-SO_2-O-C_1-C_6$-alkyl), sulfo ($-SO_3H$) or $C_1$–$C_6$-alkanesulfonyl and two of these groups can be the methylenedioxy group and X is the equivalent of a physiologically compatible anion, as well as optionally their salts with physiologically compatible cations and anions and process of their production.

7 Claims, No Drawings

TUMOR RETARDING (1-BENZYL-ETHYLENEDIAMINE)-PLATIN (II)-COMPLEXES

BACKGROUND OF THE INVENTION

It is known that compounds of the following formula

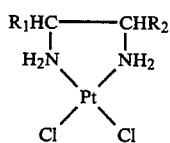

$R_1 = H$, alkyl
$R_2 = H$, alkyl have an antitumor activity (Journal of Inorganic Biochemistry, Volume 11, 1979, pages 139–149; Biochemie, Volume 60, 1978, pages 835–850). Furthermore, there are known from German Offenlegungsschrift No. 3405611 antitumor active compounds. Thereby there are described (1,2-diphenyl-ethylenediamine)-platinum (II) complex compounds of the general formula

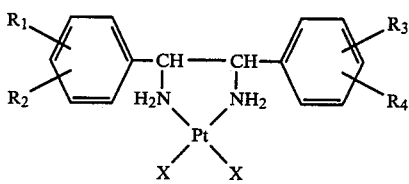

wherein the groups $R_1$, $R_2$, $R_3$, and $R_4$ are the same or different and are hydrogen, hydroxy groups, $C_1$–$C_6$-alkoxy groups, $C_2$–$C_6$-alkanoyl groups, optionally substituted by halogen atoms or $C_1$–$C_4$-alkanesulfonyloxy groups, or $C_3$–$C_6$-alkenoyloxy groups, wherein at least one of the groups $R_1$, $R_2$, $R_3$, or $R_4$ is not a hydrogen atom and X is the equivalent of a physiologically compatible anion.

The invention is directed to the subject matter defined in the claims.

SUMMARY OF THE INVENTION

There are prepared tumor retarding (1-benzyl-ethylenediamine)-platin(II)-complexes of the general formula

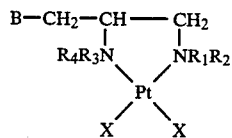

wherein the radicals $R_1$, $R_2$, $R_3$, and $R_4$ are the same or different and are hydrogen, a $C_1$–$C_6$-alkyl group, a benzyl group, or a phenylethyl group, and B is a thienyl radical, an indolyl radical, an imidazolyl radical, or a phenyl radical substituted by the radicals $R_5$, $R_6$, and $R_7$ and the radicals $R_5$, $R_6$, and $R_7$ are the same or different and are hydrogen, halogen, trihalomethyl, $C_1$–$C_6$-alkyl, hydroxy, $C_1$–$C_6$-alkoxy, phenoxy, benzyloxy, $C_1$–$C_6$-alkanoyloxy, benzoyloxy, $C_1$–$C_6$-alkanesulfonyloxy, carboxy, $C_1$–$C_6$-carbalkoxy, cyano, aminocarbonyl, aminocarbonyl, which contains one or two $C_1$–$C_6$-alkyl radicals, $C_1$–$C_6$-alkylcarbonyl, nitro, amino, $C_1$–$C_6$-alkylamino, di-$C_1$–$C_6$-alkylamino, $(C_1$–$C_6$-alkyl$)_3 N^{\oplus}$, $C_1$–$C_6$-alkanesulfonylamino, $C_1$–$C_6$-alkyl-$C_1$–$C_6$-alkanesulfonylamino, aminosulfonyl, aminosulfonyl which contains one or two $C_1$–$C_6$-alkyl radicals, $C_1$–$C_6$-alkoxysulfonyl (SO$_2$—O—$C_1$–$C_6$-alkyl), sulfo (—SO$_3$H) or $C_1$–$C_6$-alkanesulfonyl and two of these groups also can be the methylenedioxy group and X is the equivalent of a physiologically compatible anion, as well as optionally their salts with physiologically compatible cations and anions.

These compounds are produced by reacting a tetrahalo-platinum (II) acid, a tetrahalo-platinum (II) complex salt having two monovalent or one divalent cation or a platinum (II) halide with a compound of the formula

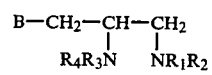     II or a salt of compound II is reacted with a physiologically compatible opposite ion or an acid addition salt of compound II, wherein the groups $R_1$, $R_2$, $R_3$, $R_4$, and B have the stated meanings, there are optionally introduced in hydroxy groups or amino groups of group B by acylation one or more $C_1$–$C_6$-alkanoyl groups, $C_1$–$C_6$-alkanesulfonyl groups or benzoyl groups, optionally amino groups present in group B are oxidized to nitro groups and optionally in a compound obtained of formula I the group X or the groups X exchanged for another physiologically compatible anion and/or optionally compounds obtained are converted into the salts with physiologically compatible anions or cations.

Medicines are prepared containing a compound of general formula (I) and in addition customary carriers and/or diluents or adjuvants.

A medicine can be produced by processing a compound of general formula I with customary pharmaceutical carriers or diluents or other adjuvants to pharmaceutical preparations or by bringing it into a therapeutically usable form.

The compounds of general formula I are used to produce medicines.

The compounds of the invention also can be administered to mammals, e.g. humans, dogs, cats, horses, and cattle in an amount effective to retard the growth of a tumor.

The new compounds of the invention have a decided antitumor activity together with good compatibility. The action is shown especially in the following animal and cell culture models:

Mouse leukemia P388, mouse leukemia L1210, cis-platinum sensitive reticular mouse cell sarcoma M5076, hormone independent human breast cancer cell line MDA-MB 231.

The compounds of the invention prevent or retard both the growth of tumor cells present and also the formation of new tumor cells; furthermore they destroy tumor cells present or lead to their regression and prevent or weaken the formation of metastases.

In comparison to the known compounds the compounds of the invention at comparable or superior activity are considerably less toxic.

The following data is directed to the preferred illustration of the invention.

The $C_1$–$C_6$-alkyl groups, the alkoxy groups present and the $C_1$–$C_6$-alkanoyloxy groups can be straight or branched and preferably consist of 1 to 4 C-atoms. The same is also true if the $C_1$–$C_6$-alkyl groups are components of other functional groups (for example in the case of $C_1$–$C_6$-alkanesulfonyloxy or $C_1$–$C_6$-alkylaminocarbonyl etc.). As alkanoyloxy groups there is especially employed the acetoxy group. As halogen substituents there are especially employed bromine, chlorine and/or fluorine. With the trihalomethyl group there is preferably used trifluoromethyl. Preferably the thiophene group is a thienyl-(2)-group, the indole group is preferably an indolyl-(3)-group and with the imidazole group the imidazolyl-(4)-group. In case one or more of the groups $R_1$, $R_2$, $R_3$, or $R_4$ is an alkyl group, preferably it is a methyl group, an ethyl group or an isopropyl group. In the case of the phenylethyl group it is preferably the 1-phenylethyl group. With the $C_1$–$C_6$-alkyl-$C_1$–$C_6$-alkanoylamine group there is employed an amino group which contains on the nitrogen the $C_1$–$C_6$-alkyl group and the $C_1$–$C_6$-alkanoyl group. The analogous is true in the case of the $C_1$–$C_6$-alkyl-$C_1$–$C_6$-alkanesulfonylamino group.

Those compounds of formula I wherein B is a monochlorophenyl group, for example a 4-chlorophenyl group, have an especially favorable action.

In case one or more of the groups $R_5$, $R_6$, and $R_7$ contains a carboxy group or a sulfo group the compounds of formula I can also be present in the form of the corresponding salts with physiologically compatible cations. As such cations there can be used cations of the alkali metals (Na, K), the alkaline earth metals (Ca, Mg), cations of aliphatic mono-, di-, tri-. or quaternary $C_1$–$C_6$-alkylamines which also can be substituted by phenyl, $NH_4^\ominus$.

In case one or more of the groups $R_5$, $R_6$, or $R_7$ represents an ammonium group or the group ($C_1$–$C_6$-alkyl)$_3N^\ominus$, the compounds of formula I are present in the form of the salts with physiologically compatible anions. Hereby there are employed for example those anions which also are employed for group X.

The group X represents the known and customary physiologically compatible and pharmaceutically usable anions of mono or polyvalent acids. For example, there are used the anions of the following acids:

HBr, HCl, HI, HF, $HNO_3$, $H_2SO_4$ ($SO_4^{--}$); $H_3PO_4$ ($HPO_4^{--}$); $H_2CO_3$, ($CO_3^{--}$); camphorsulfonic acid, aliphatic or aromatic sulfonic acid, for example $C_{1-C_6}$-alkylsulfonic acid (for example methanesulfonic acid, ethane-, propane- or hexanesulfonic acid), benzene- or naphthalenesulfonic acid, which optionally are substituted once or twice by methyl groups (toluenesulfonic acid, especially o- or p-toluenesulfonic acid); aliphatic $C_1$–$C_4$-monocarboxylic acid, which optionally are substituted once, twice, or three times by halogen atoms (especially Cl, F) (for example formic acid, acetic acid, propionic acid, chloroacetic acid, dichloroacetic acid, trifluoroacetic acid, trichloroacetic acid); aliphatic $C_2$–$C_{11}$ dicarboxylic acids, which optionally contain a double bond (for example oxalic acid, malonic acid, 2-aminomalonic acid, malonic acid which is substituted in the 2-position by a benzyl group or one or two $C_1$–$C_4$-alkyl groups, maleic acid, fumaric acid, succinic acid); aliphatic monohydroxy- and dihydroxy-monocarboxylic acids having 2 to 6, especially 2 to 3 carbon atoms, in which case they are preferably α-monohydroxycarboxylic acids such as lactic acid, glyceric acid, or glycolic acid, aliphatic monohydroxy- and dihydroxy- di- and tricarboxylic acids having 3 to 8 carbon atoms, especially 3 to 6 carbon atoms, such as malic acid, tartaric acid, malonic acid which is substituted on the middle carbon atom by a hydroxy group and optionally can be substituted by a $C_1$–$C_4$-alkyl group, isocitric acid or citric acid, phthalic acid which optionally is substituted by a carboxy group (especially in the 4-position); gluconic acid; glucuronic acid; the natural α-aminoacids (for example L-aspartic acid); 1,1-cyclobutanedicarboxylic acid; organophosphoric acids, such as aldose and ketose phosphoric acids, (for example the corresponding mono- and diphosphoric acids) for example aldose-6-phosphoric acids such as D- or L-glucose-6-phosphoric acid, α-D-glucose-1-phosphoric acid, D-fructose-6-phosphoric acid, D-galactose-6-phosphoric acid, D-ribose-5-phosphoric acid, D-fructose-1,6-diphosphoric acid; glycerine phosphoric acids (whereby the phosphoric acid residue is connected on one of the end or on the middle glycerine oxygen atom) such as α-D,L-glycerine phosphoric acid, β-glycerine phosphoric acid, N-phosphono-acetyl-aspartic acid.

As acids for the anion X additionally there can be used aromatic carboxylic acids which contain one or more carboxy group as well as additionally $C_1$–$C_4$-alkoxy groups and/or hydroxy groups. In case several carboxy groups are located on the aromatic radical (for example a benzene ring), preferably at least 2 carboxy groups are in adjacent positions. In case the benzene ring for example contains 4 or 5 carboxy groups, complexes can form, which contain per mole of the benzenecarboxylic acid anions 2 moles of the platinum component. 2 adjacent carboxy groups neutralize at a time 1 mole of the platinum component, so that for example, in the case of benzenepentacarboxylic acid the 1 and 2 position as well as the 4 and 5 position carboxy groups at a time saturates 1 mole of the platinum component (thus together 2 moles), while the free carboxy group in the 3 position is free or in the salt form with a physiologically compatible cation (for example alkali cation, especially sodium cation). This is generally true if the anions X still have additional acid functions which are not used for saturation of the platinum. The analogy is true in the case of benzenehexacarboxylic acid, in which case here optionally 1 mole of this acid can saturate 3 moles of the platinum component.

Examples of such acids are benzene-monocarboxylic acid, benzene dicarboxylic acids, benzene tricarboxylic acids, (for example trimellitic acid), benzene tetracarboxylic acid, benzene pentacarboxylic acid, benzene hexacarboxylic acid, syringic acid, orotic acid.

Likewise there can be used as acids which form the anions X aminoacids or aminoacid derivatives whose basic amino group is neutralized by an acid group. Thereby there can be used for examples aminoacids of the following structure:

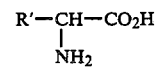

wherein R′ is hydrogen, a phenyl radical, an indolyl-(3)-methyl radical, imidazolyl-(4)-methyl radical, a $C_1$–$C_{10}$-alkyl group or a $C_1$–$C_{10}$-alkyl group which is substituted by a hydroxy group, a carboxy group, a $C_1$–$C_6$-alkoxy group, a mercapto group, a $C_1$–$C_6$-alkylthio group, a phenyl group, a hydroxyphenyl group, a $C_2$–$C_6$-alkanoylamino group or a $C_1$–$C_6$-alkoxycarbonyl group.

The basic amino group in the 2-position hereby is neutralized (acylated) by a customary aminoacid protective group, for example by a $C_2$–$C_6$-alkanoyl radical or the butyloxycarbonyl radical.

In case in the above formula R' is an alkyl group it is preferably a $C_1$–$C_6$-alkyl group which for example contains in the 2-, 3-, 4-, 5-, or 6-position (counting begins at the position of connection of the alkyl group to the rest of the molecule), a $C_2$–$C_6$-alkanoylamino group, an imidazolyl-(4)-methyl radical or an indolyl-(3)-methyl radical. Individual examples of such aminoacids are asparagine (preferably D- and L-form), lysine (preferably D- and L-form), tryptophane (preferably D- and L-form), tyrosine (preferably D- and L-form), ornithine (preferably D- and L-form).

Thereby the basic amino groups are blocked by a customary acylamino protective group, especially by the acetyl group or the butyloxycarbonyl group.

Formula I also embraces the possible enantiomers and diastereomers. In case the compounds are racemates these can be resolved in known manner, for example by means of an optically active acid into the optically active isomers. However, it is also possible from the outset to employ enatiomers or optionally also diastereomeric starting materials, in which case then as end product there is obtained a corresponding pure optically active or diastereomeric compound. Independent of the structure of the radical X the L-benzylethylenediamine portion has 1 asymmetric carbon atom and therefore can be present in the racemate form or in the levorotatory or dextrorotatory form. Additionally forms can arise through different enantiomeric or diastereomeric forms of the radical X.

In regard to the platinum atom the compounds of the invention of formula I always are the cis-compounds.

The starting amine II is employed for example as the racemate, as pure dextrorotatory or levorotatory form or in another diastereomeric form.

This configuration remains in the production of the platinum complex.

The process for the production of the compounds I of the invention is carried out in a solvent at temperatures between 0° and 90° C., preferably 10° to 60° C., especially 20° to 50° C. As solvents there can be used for example water, $C_1$–$C_6$-alkanols (methanol, ethanol, tert.butanol), tetrahydrofuran, dioxan, dimethylsulfoxide, dimethylformamide, ethyleneglycoldimethylether, diethyleneglycoldimethylether as well as mixtures of the solvents, especially mixtures with water.

The two reactants (platinum compound and compound II) are preferably employed in equimolar amounts. The pH of the reaction solution should be between 5 and 7, preferably at 6. The regulation of the pH is carried out especially by addition of alkali, preferably aqueous sodium hydroxide or potassium hydroxide or for example also by means of sodium carbonate or by the addition of acids, preferably aqueous hydrochloric acid.

As tetrahalogen-platinum (II) compounds (acids as well as complex salts) there are employed the corresponding tetrachloro-, tetrabromo-, and tetraiodo compounds. In the event platinum (II) halide is employed as starting component the same halogen atoms are used.

As monovalent cations there are used alkali ions, especially sodium and potassium; however, there can also be used lithium, rubidium, cesium, likewise $NH_4^\oplus$, $NR_4^\oplus$, $PR_4^\oplus$, or $AsR_4^\oplus$ in which R is a $C_1$–$C_6$-alkyl radical or a phenyl radical. Divalent cations can be alkaline earth ions, especially $Mg^{2+}$ and $Ca^{2+}$, as well as $Zn^{2+}$. As platinum (II) halides there can be used for example $PtCl_2$, $PtBr_2$, and $PtI_2$.

The compound II is employed either in the form of the diamine or in the form of an acid addition salt: for example, as the monohydrochloride or dihydrochloride, mono- or dihydrobromide, mono- or dihydroiodide or as the salt with another customary acid. Especially there can be used acids whose anions form the radical X. Furthermore, the diamine can be employed in the form of the acetate or diacetate, in which case optionally before mixing the reactants there is added potassium chloride (for example 2 moles per mole of compound II). Likewise the diamine II can be employed in the form of the carbonate.

In compounds of formula I hydroxy groups and/or amino groups or $C_1$–$C_6$-alkylamino groups of the radical B can be acylated by $C_1$–$C_6$-alkanoyl groups or by $C_1$–$C_6$-alkanesulfonyl groups. In the same way the benzoyl group can also be introduced into hydroxy groups of radical B. This acylation can be carried out for example by means of a phosgene, $C_1$–$C_6$-alkanesulfonyl halides or the anhydrides of saturated aliphatic $C_1$–$C_6$ monocarboxylic acids at temperatures between 10° and 80° C., especially 20°–30° C. in the presence of customary acid binding materials. Especially there can be used as acid binding materials aliphatic tertiary amines such as for example diisopropyl ethyl amine. As inert solvent or suspension agents for the acylation there can be used for example lower aliphatic halohydrocarbons (chloroform), aprotic solvents such as amides, $C_1$–$C_4$-alkylamides and $C_1$–$C_4$-dialkylamides of aliphatic $C_1$–$C_4$-carboxylic acids (dimethyl formamide, dimethyl acetamide), N-methylpyrrolidone, dimethyl sulfoxide or mixtures of these agents.

However, this acylation can also be carried out in a two phase system, for example water/chloroform, in which case the acylated platinum (II) complex obtained with the help of an anion exchanger separates as insoluble and the mixture of acid chloride and tertiary amine (diisopropyl ethyl amine) is found in the chloroform phase. As acid halides there are preferably used the corresponding chloride, bromide and optionally iodide. As anhydride there can be used benzoic anhydride as well as anhydrides of $C_1$–$C_6$-carboxylic acids, for example symmetrical acid anhydrides such as acetic anhydride, propionic anhydride, butyric anhydride.

The exchange of the ligands X against other ligands for example can be carried out by means of silver halide precipitation. For this purpose for example a dihalo-(1)-benzylethylenediamine)-platinum-(II)-compound of formula I, wherein X is halogen (chlorine, bromine, or iodine) is reacted in a solvent or suspension agent at temperatures between 0° and 90° C., preferably 10° to 50° C., especially 30° to 40° C., preferably 40° C. with thes silver salt of another acid, which corresponds to the definition of X. However, thereby there can also be used as the silver salt silver nitrate (for example aqueous silver nitrate solution) and there is obtained an ionic diaquo complex of the formula

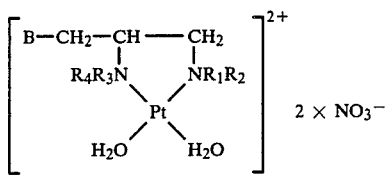

The weakly bound ligand water is readily replaced from this complex by more affin anions (for example $Cl^-$, $Br^-$ in the form of NaCl, KCl, NaBr, KBr, $malonate^{2-}$, $chloroacetate^\ominus$, $oxalate^{2-}$-1,1-cyclobutanecarboxylic acid $anion^{2-}$ as well as the rest of the stated acid radicals X used in the form of acids or their salts, especially their alkali salts, (e.g. sodium or potassium salts).

The same compounds can also be obtained by reaction of equimolar amounts of HX and nitrate free platinum complex (the latter using anion exchangers in the hydroxide form, for example Dowex 1-8X).

An exchange of the leaving group (for example $SO_4^{2-}$ or oxalate $anion^{2-}$) is also possible in the case of the sulfato or oxalato-(1)-benzylethylenediamine)-platinum (I) compounds by reaction with alkaline earth salts (e.g. calciums salts) which contain the desired X-ligands (for example glyceric acid), insofar as the complex formed is water soluble and therewith permits the separation of the difficultly water soluble alkaline earth sulfate or oxalate.

Suitable X-ligands for this process are preferably the anions of hydroxycarboxylic acids, sulfonic acids, haloacetic acids, nitric acid.

The solvent or suspension agents which have been given for the process of production of the compounds I also can be used for the exchange reaction (especially suited are water and dimethyl formamide as well as also methanol, ethanol, tert.butanol). The exchange reaction is carried out for example in the pH range between 3 and 7.

Production of Starting Materials of Formula II wherein B is an Optionally Substituted Phenyl Radical or a Heterocyclic Radical Permitted for B The production of these compounds (optically active compounds and racemates) can be carried out for example analogously to the known production of benzylethylene-diamine (D and L-form, racemate) according to the following stereospecific synthesis:

Esterification of the phenylalanine correspondingly substituted in the phenyl nucleus or the alanine substituted in the $\beta$-position by a thiophene radical, indole radical or imidazole radical (D- or L-form or racemate) by reflux boiling with thionyl chloride in methanol. The methyl ester is obtained as the hydrochloride (Helv. Chim. Acta 39, 1421 (1956)). Repeated saturation of the methanolic solution with ammonium at $-5°$ C. to $0°$ C. leads to the corresponding amides (J. Amer. Chem. Soc. 53, 3183 (1931); J. Biol. Chem. 199, 801 (1952); Inorg. Chem. 18, 206 (1979)), in which case the hydrogen chloride of the ester-hydrochloride remains partially bound on the amide. A portion also precipitates as ammonium chloride under the reaction conditions, which can be separated off by fractional crystallization. In the third reaction step $\alpha$-aminoacid amide is reduced to the diamine. This occurs by addition of solid amide to a suspension of lithium aluminum hydride in tetrahydrofuran, reflux boiling and subsequent hydrolysis (Helv. Chim. Acta 38, 2036, (1955); Inorg. Chem. 18, 206, (1979); Gazz. Chim. Ital. 85, 1354, (1955); Bull. Chem. Soc. Jap. 49, 101, (1976) or to $Al(BH_4)_3$ in dioxan (produced in situ from $NaBH_4$ and $AlCl_3$; see J. Am. Chem. Soc. 78, 2582, (1956)). The hydrolysis products of the lithium aluminum hydride are filtered off and the diamine isolated as a viscous oil by drawing off the solvent. The diamine can be obtained in pure form by distillation under reduced pressure or converted into the hydrochloride by reaction with concentrated hydrochloric acid or with etheric hydrochloric acid.

This process can be carried out for example analogous to the manner described in the dissertation of Manfred Schmidt, 1984, University of Regensburg, pages 119-122.

The substituted phenylalanine employed for this synthesis procedure be obtained in the following manner:

In the first step in an "Azlactone Synthesis according to E. Erlenmeyer jun," the benzaldehydes substituted by the radicals $R_5$, $R_6$ and $R_7$ are condensed with N-acetyl- or N-benzoylglycine by heating under the influence of sodium acetate in acetic anhydride to the unsaturated azlactones (oxazolones) (Org. React. 3, 198 (1946)).

The second step, the conversion of the azlactone into the corresponding $\alpha$[N-acylamino]cinnamic acid is carried out in two steps, namely via a saponification with dilute aqueous sodium hydroxide and subsequent precipitation with dilute hydrochloric acid. Thereby it is important to avoid both strong acid (J. Amer. Chem. Soc. 64, 885 (1942)) or basic conditions (J. Biol. Chem. 82, 438 (1929)) as well as long heating (J. Biol. Chem. 82, 438 (1929)), since otherwise the $\alpha$[N-acylamino]cinnamic acids primarily formed are hydrolyzed to $\alpha$-ketoacids. Because of the high stability of the unsaturated azlactone, especially the 2-phenylazlactone, these conditions cannot be avoided which in a given case is reflected in lower yields.

In the third reaction step the cinnamic acids are reduced to the benzoyl- or acetyl-aminoacids. For this purpose the cinnamic acids are suspended in water and treated at room temperature with solid sodium amalgam (Berichte Dtsch. Chem. Ges. 3638 (1899). The acetyl- or benzoyl-aminoacids thereupon, after decanting the solution formed from mercury, can be precipitated with hydrochloric acid.

The hydrolysis of the N-benzoyl group or the N-acetyl group in the last reaction step is attained by boiling the acids for several hours in 20% hydrochloric acid. The substituted amino acids then precipitated after addition of ammonia up to a weakly acid pH region. They can be recrystallized by dissolving in acid and precipitation with ammonia or sodium acetate.

This process for example can be carried out analogous to the method described in the dissertation of Manfred Schmidt, 1984, University of Regensburg, pages 111-114.

Another way is the following:

In this synthesis reduced to two steps the benzaldehyde substituted by the radicals $R_5$, $R_6$, and $R_7$ is reacted with hydantoin (molar ration 1:1) and molten, anhydrous sodium acetate at 160° C. within 15 hours nearly quantitatively to the corresponding benzalhydantoin. This stable, mostly yellowish solid is converted directly into the $\alpha$-aminoacids by reduction and simultaneous breaking of the ring with ammonium sulfide at 100° C. in a moving autoclave within 60 hours.

This process for example can be carried out analogous to the method described in the dissertation of Manfred Schmidt, 1984, University of Regensburg, pages 116–119.

The starting aldehydes employed hereby can be obtained for example from the benzene derivatives substituted by the radicals $R_5$, $R_6$, and $R_7$ by the following known reaction: By treatment with paraformaldehyde in concentrated hydrochloric acid a chloromethyl group is introduced, then the chloromethyl group is hydrolyzed by means of aqueous sodium hydroxide to the hydroxymethyl group (in the event mixtures of isomeric hydroxymethyl compounds are formed thereby, these can be separated chromatographically, for example with $CH_2Cl_2$/ether 1:1), subsequently then the hydroxymethyl group is oxidized by means of freshly precipitated active manganese dioxide to the aldehyde group.

This process for example can be carried out analogous to the method described in the dissertion of Manfred Schmidt, 1984, University of Regensburg, pages 115–116.

Benzylethylenediamines which contain free hydroxy groups in the phenyl nucleus are suitably obtained from the corresponding benzylethylenediamines, in which one or more of the readicals, $R_5$, $R_6$, and $R_7$ are methoxy groups (which can be produced in the manner previously stated) by ether cleavage with boron tribromide, for example in methylene chloride suspension at $-60°$ C. (E. van Angerer, Habilitation Thesis, University of Regensburg 1983). Suitably the thus obtained dihydrobromides of the hydroxy compounds after liberating the amines in methanol or ethanol are converted with etheric hydrochloric acid or in ether with hydrogen chloride gas into the corresponding dihydrochlorides of the diamine II, wherein B is the phenyl group substituted by the radicals $R_5$, $R_6$, and $R_7$ and in this case at least one of the radicals $R_5$, $R_6$, and $R_7$ represents a hydroxy group.

The diamine II, in which $R_1$ or $R_1$ and $R_2$ are $C_1$–$C_6$-alkyl groups, benzyl groups or phenylethyl group are obtained from the corresponding α-aminoacidamides, in which preparation in place of ammonia there is used a $C_1$–$C_6$-alkylamine, a $C_1$–$C_6$-dialkylamine, benzylamine or phenylethyl amine. Thereby it is advantageous in a given case to protect the α-amino group of the α-aminoacid employed with a customary protective group (for example the benzyloxycarbonyl radical). The reaction of the protected α-aminoacid thus obtained with the amine $HNR_1R_2$ is carried out suitably in known manner in the presence of N-hydroxysuccinimide and dicylohexylcarbodiimide.

The α-amino-protective group then before the reduction with $LiAlH_4$ is cleaved acidolytically in known manner (for example with saturated hydrogen bromide solution in glacial acetic acid). If in contrast in the case of the benzyloxycarbonyl radical (as protective group for the α-amino group) this is not cleaved beforehand, but the protected acid amide is reduced directly with $LiAlH_4$, there is obtained the corresponding amine of formula II, wherein $R_3$ is a methyl group ($R_4=H$; $R_1$, $R_2=H$, $C_1$–$C_6$ alkyl, benzyl or phenylethyl). Amines of the formula II, wherein $R_3$ and/or $R_4$ are $C_1$–$C_6$-alkyl groups ($R_1$ and $R_2$ have the meanings given for them) for example can be obtained in known manner also by mono- and dialkylation of the corresponding acid amide of the formula

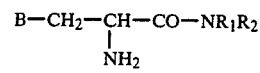

and subsequent reduction with $LiAlH_4$. To produce the diamine II in which $R_3$ or $R_3$ and $R_4$ or $R_1$ and $R_3$ are methyl groups, the corresponding α-aminoacid amide or the corresponding diamine is mono- or dimethylated for example with methyl chloroformate (Bull. Chem. Soc. Jpn 53, 2275 (1980)) or by reductive alkylation with formaldehyde in the presence of formic acid (Org. Synth. Coll., Volume III, 723), whose reduction with lithium aluminum hydride in customary manner (for example according to the dissertation of Manfred Schmidt, University of Regensburg, 1984, page 121) gives the N-substituted diamine II. In this reaction simultaneously the methyl formate radical is simultaneously converted into a methyl group. To introduce four methyl groups in the position $R_1$, $R_2$, $R_3$, and $R_4$ the diamine II with $R_1$, $R_2$, $R_3$, $R_4=H$ is reductively alkylated with formaldehyde/formic acid (Org. Synth. Coll., Volume III, 723).

Diamines II in which $R_1$ and $R_3$ are isopropyl groups are synthesized for example by converting them in known manner with acetone into the Schiff bases and reducing these with sodium borohydride. An isopropyl group can also be introduced in the $R_3$ position by condensing the amino group of the α-aminoacids with acetone and converting this derivative in the described manner with lithium aluminum hydride into the diamine II (see dissertation of Manfred Schmidt, 1984, University of Regensburg, pages 119–122). Thereby the imino group is reduced to the N-isopropyl group. Correspondingly benzyl or phenylethyl groups are introduced on the position $R_3$ by condensing the α-aminoacid derivative with benzaldehyde or acetophenone and subsequently reducing with $LiAlH_4$.

The production of those diamines of formula II wherein B represents one of the stated heterocyclic radicals can be carried out according to preceding methods from the corresponding heterocyclic aldehydes (for example thienyl-(2)-aldehyde) or the corresponding heterocyclic aminoacids (that is derivatives of alanine, in which case the alanine is substituted in the β-position by the corresponding heterocyclic residue).

$C_1$–$C_6$-alkanoyl groups can be introduced into OH groups or amino groups which are located on the phenyl radical of the diamine II by acylation (Phenolic hydroxy groups can also be converted into benzoyloxy groups.) Acylation reagents thereby are acid halides of aliphatic $C_1$–$C_6$-carboxylic acids, preponderantly acid chlorides as well as benzoyl chloride for the $C_6H_5COO$-substituents. Also, there can be used the corresponding acid anhydride, for example acetic anhydride to form the $CH_3COO$-substituents. The $C_1$–$C_6$-alkanesulfonyl-substituents are introduced correspondingly, the latter for example with the help of the corresponding sulfonic acid chloride. In these acylations the two aliphatic amino functions are suitably protected by imine formation, for example with benzaldehyde. After the acylation the imino group can be cleaved again into the amino group, for example by hydrolysis with dilute HCl.

To manufacture compounds which have a carboxyl function or a carbonyl function in the radical B the corresponding methylenoxy-alkyl compounds are the starting material. The ether bond in the $CH_2OCH_3$-substituents remains unchanged during the entire synthesis. At the stage of the diamine II there is carried out the ether cleavage to the $CH_2OH$— compound, as described. With strong oxidation agents, for example with $CrO_3$, the $CH_2OH$ group can be converted into the carboxyl group. The carboxyl group can be changed by neutralization with bases into carboxylate salts of physiologically compatible cations, for example with alkali hydroxides, especially NaOH, KOH or alkaline earth hydroxides, especially $Mg(OH)_2$, $Ca(OH)_2$. In place of the alkali- and alkaline earth hydroxides there can also be used other alkaline reacting materials, for example the carbonates. Also there can be introduced the ammonium ion $NH_4^\oplus$ as well as substituted ammonium ions $NR_4^\oplus$ (R=hydrogen, $C_1$-$C_6$-alkyl, phenyl or benzyl) either by reaction of the carboxyl compounds with the corresponding amines or through ion exchange with ion exchangers in the $NR_4^\oplus$-form.

With the help of $C_1$-$C_6$ alcohols (e.g. methanol, ethanol, hexanol) the carboxyl groups can be esterified and converted into the corresponding acidamides by reaction with ammonia or amines $NR_3$ ($R_3$=hydrogen, $C_1$-$C_6$-alkyl). Through the effect of water removing materials, for example $P_2O_5$, there is formed the cyano group from the carbonylamino group.

In the careful oxidation of the compounds of Type II with $CH_2OH$ groups obtained as described above, for example according to Oppenauer with acetone/aluminum isopropoxide, there are formed formyl derivatives. If there is used in the manufacture the ether substituent $CHR$—$O$—$CH_3$ ($C$=$C_1$-$C_6$-alkyl) then the corresponding compounds can be changed through ether cleavage and oxidation of the alcoholic group formed into the $C_1$-$C_6$-carbonyl substituent compounds.

Amino substituents $NR_2$ (R=hydrogen, $C_1$-$C_6$-alkyl) are introduced by beginning the synthesis of diamines II with the corresponding amino substituents, which substituents, however, insofar as they still contain NH-bonds are protected by benzoylation, for example with benzoyl chloride. The benzoyl groups on the amino substituents are indeed reduced during the $LiAlH_4$ reduction to benzyl groups. However, this can be split off hydrogenolytically, for example under the influence of water with the help of the catalyst platinum on carbon.

The NH— group of the amino substituents can be converted into NR— group (R=$C_1$-$C_6$-alkyl) by alkylation. By exhaustive alkylation, for example with dimethyl sulfate, or by acidification with strong acids such as hydrochloric acid or sulfuric acid, all amino substituents $NR_2$ can be converted into the corresponding ammonium substituents $NR_3^\oplus$ in which R can be hydrogen, $C_1$-$C_6$-alkyl. Amino groups $NH_2$ and NHR (R=$C_1$-$C_6$-alkyl) which still contain one or two H-atoms can be converted into the monoacylated substituent NHCOR' and NRCOR' (R'=$C_1$-$C_6$-alkyl) can be converted by acylation, as described with the OH— compounds. This occurs after production of the complex I in which the coordinated $NH_2$ groups of the ethylenediamine portion of the molecule has a greatly reduced reactivity to acylation agents. Instead of acylation sufonylation agents also can be employed with formation of the $C_1$-$C_6$-alkanesulfonyl groups.

The oxidation of an amino group on the aromatic ring of the benzyl radical B can be carried out with the help of the methods stated in Houben-Weyl, Methoden der Organischen Chemie, Stickstoffverbindungen I, Part I, Thieme-Verlag Stuttgart 1971, pages 843-849, for example with per acids, such as peroxydisulfuric acid (for example ammonium peroxydisulfate), peroxymonosulfuric acid, peroxyacetic acid, peroxytrifluoric acetic acid, peroxymaleic acid. The reaction can be carried out for example in sulfuric acid, glacial acetic acid or halogenated hydrocarbons ($CH_2Cl_2$) at temperatures between 10°-50° C., preferably 10°-80° C., especially 10°-20° C.

The sulfo group survives in the form of the $SO_3$— anion the reaction steps leading to the diamines II and the platinum complexes I. They can be converted into the $SO_3H$ form by acidification with strong acids. Additions of bases or alkaline reacting materials gives the corresponding sulfonate with physiologically compatible cations (analogous to the carboxylates). Esterification of the sulfo group with $C_1$-$C_6$-alcohols or amidation with ammonia, primary amines $RNH_2$ and secondary amines $R_2NH$ (R=$C_1$-$C_6$-alkyl) in the step to the diamine II lead to sulfonic acid esters and sulfonic acid amides having the substituents $SO_3R$, $SO_2NH_2$, $SO_2NHR$, $SO_2NR_2$.

The $C_1$-$C_6$-alkanesulfonyl groups, present in the benzaldehyde at the beginning of the reaction are not attacked in the reactions forming the diamine II and the platinum complex I.

Unless otherwise indicated all parts and percentages are by weight.

The composition can comprise, consist essentially of, or consist of the stated materials and the processes can comprise, consist essentially of, or consist of the recited steps with such materials.

DETAILED DESCRIPTION

For further illustration reference is made to the production of several starting compounds of formula II in connection with Examples 17-25 as well as to the diploma work of Ulrich Holzinger "Synthese und Untersuchung von N-alkyl substituierten tumorhemmenden 1,2-Diamino-3-phenylpropan-dichloroplatin(II)-Komplexen", Division of Chemistry-Pharmacy of the University of Regensburg, 1985. The production of other starting materials can be carried out in analogous manner.

The starting compound II, wherein B is the 4-chlorophenyl radical and the radicals $R_1$, $R_2$, $R_3$, and $R_4$ are hydrogen can be produced for example as follows (the production of other corresponding starting materials can be carried out analogously):

4-Chlorophenylalanine Methyl Ester Hydrochloride 0.14 mol (10 ml, 16.5 grams) of thionyl chloride were dropped at $-5°$ C. into 100 ml of methanol. After addition of 0.11 mole (22 grams) of 4-chlorophenylalanine the mixture was heated under reflux for 15 hours. After drawing off the solvent the white residue was dried in a high vacuum.

The reaction takes place quantitatively. The formation of ester can be followed IR-spectospecially on the appearance of a band at about 1750 cm$^{-1}$. The product is employed without further purification in the next step.

4-Chlorophenylalanineamide 0.1 mole (25 grams) of 4-chlorophenylalanine methyl ester hydrochloride were dissolved in 250 ml of methanol. Then ammonia was led in at 0° C. several times, each time up to saturation. The reaction was finished after 4 days. The solvent was drawn off and the white residue dried. The product was employed in this form in the next step.

1,2-Diamino-3-(4-chlorophenyl)propane 0.1 mole (20 grams) of 4-chlorophenylalanineamide or hydrochloride were added in small portions to a well stirred suspension of 0.3 mole of LiAlH$_4$ in 250 ml of dry tetrahydrofuran. The mixture was stirred for 24 hours under reflux and subsequently under ice cooling hydrolyzed dropwise with 1.2 moles of H$_2$O. After stirring at room temperature for an additional hour it was filtered off from the hydrolysis products accumulating as a slime-like solid. This residue was extracted for 24 hours with 127 ml of tetrahydrofuran. Filtrate and extract were combined.

1,2-Diamino-3-(4-chlorophenyl)propane-Dihydrochloride (Starting Material II)

The production can be carried out according to two different methods:

(a) The combined tetrahydrofuran solutions (filtrate and extract) were concentrated to half the volume and subsequently treated under ice cooling dropwise with concentrated HCl. The dihydrochloride which precipitated was filtered off and dried.

(b) The combined tetrahydrofuran solutions were concentrated and the oily residue dissolved in 5-10 ml of absolute ethanol. Thereupon it was treated dropwise under ice cooling and vigorous stirring with 20 ml of etheric hydrochloric acid. After addition of 20 ml of ether at $-40°$ C. the dihydrochloride separated out as a fine, white solid, (M.P. 249°-252° C., decomposition from 240° C.).

The compounds of the invention are suited for the production of pharmaceutical compositions. The pharmaceutical compositions or medicaments can contain one or more of the compounds of the invention as well as mixtures of the same with other pharmaceutically active materials. For the production of the pharmaceutical preparations there can be used the customary pharmaceutical carriers and adjuvants. The medicines can be used for example enterally, parenterally (for example intravensusly, intramuscularly, subcutaneously) or orally. For example the dispensation can be carried out in the form of tablets, capsules, pills, dragees, or plugs. As liquids there can be used for example: oily or aqueous solutions or suspensions (for example in sesame or olive oil), emulsions, injectable aqueous and oily solutions or suspensions. Furthermore, there can be produced for example dry ampoules which contain as active material the compound I of the invention, in which case before use the contents of such dry ampoules can be dissolved for example in physiological salt solution or mixtures of physiological salt solution and, for example, dimethyl sulfoxide.

The compounds of the invention for example show a good antitumor activity in the M 5076 reticulum cell sarcoma (mouse), on the P388 leukemia (mouse), on the L 5222 leukemia (rat) and on the human MDA-MB 231 breast cancer cell line. For example with the compound according to Example 4 with the reticulum cell sarcoma (mouse) with subcutaneous dispensation with a dosage of 30.0 mg/kg (body weight) mouse there is attained a retrogression of the size of the starting tumor. In the testing on the hormone independent human mammary tumor cell line MDA-MB 231 (see Dissertation of Manfred Schmidt, University of Regensburg, 1984, pages 78, 168 et seq.). the compounds of the invention in vitro show for example in concentrations between $1-5\times10^{-6}$ mole/liter, especially $1.3-2.5\times10^{-6}$ moles/liter a 50% retardation of growth on this cell line. The retardation of the incorporation of [$^3$H]-thymidine is of the same order of magnitude. In the cell culture experiments with the mouse leukemia L 1210 the compounds of the invention for example show a 50% retardation of growth in dosages between 0.01-0.2 μg/ml.

The positive effect of the compounds of the invention is comparable with the known agent cisplatin. However, with the compounds of the invention for example the toxic side effects are reduced considerably.

The lowest already effective dosage on the reticulum cell sarcoma of the mouse for example is 5×3.2 mg/kg intraperitoneally. As general dosage range for the effect (reticulum cell sarcoma/mouse) there can be used: 3.2-30.0 mg/kg intraperitoneally or intravenously, especially 15 mg/kg.

Indications for the compounds of the invention can include: tumor illnesses, especially mammary carcinoma, leukemia, reticulum cell sarcoma, furthermore ovarial, prostate, and endometrium sarcomas.

The pharmaceutical preparations generally contain between 100 to 200, preferably 150 mg of the active components of the invention.

The dispensation for example can be carried out in the form of tablets, capsules, pills, dragees, plugs, salves, jellies, creams, powders, dusts, aerosols, or in liquid form. As liquid forms of use there can be employed: oily or alcoholic respectively aqueous solutions as well as suspensions and emulsions. Preferred forms of use are tablets which contain between 100 and 200 mg or solutions which contain between 0.02 to 0.04% of active material.

The individual dosage of the active components of the invention for example can be:

(a) with oral forms of the medicine between 100 to 200 mg, preferably 150 mg;

(b) with parenteral forms of the medicine (for example intravenously, intramuscularly), between 100 to 200 mg/m$^2$ body surface area, preferably 150 mg/m$^2$ body surface area;

(c) with forms of medicine for rectal or vaginal application between 1 to 5%, preferably 2.5%, (d) with forms of the medicine for local application to the skin and mucosa (for example in the form of solutions, lotions, emulsions, salves etc.) between 1 to 5%, preferably 2.5%.

(The dosages in each case are based on the free base.)

For example, there can be recommended 3 times daily 1 to 4 tablets having a content of 100 to 200 mg of active material or for example with intravenous injection 1000 ml having an active material content corresponding to 100 to 200 mg/m$^2$ body surface area. With oral dispensation the minimum daily dosage for example is 300 mg; the maximum daily dosage with oral dispensation should not exceed 800 mg.

The acute toxicity of the compounds of the invention on the mouse (expressed by the LD$_{50}$ mg/kg; method of Miller and Tainter; Proc. Soc. Exper. Biol. a Med. 57 (1944) 261) for example with intraperitoneal application is 464 mg/kg.

The medicine can be used in human medicine and in veterinary medicine alone or in admixture with other pharmacologically active materials.

EXAMPLES

General Procedure for the Production of Cis-Diamino-Dichloro-Platinum II-Complexes of the Formula:

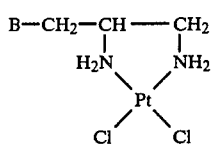

wherein B has the meanings set forth above.

EXAMPLES 1 TO 16 OF TABLE 1

1 mmole (415 mg) of potassium tetrachloroplatinate (II) is dissolved in 5 ml of water. The reaction flask is protected against light leaks with aluminum foil. A solution of 1 mmole of the compound II (as di- or mono-hydrochloride) in 5 ml of water is dropped in under stirring at room temperature. The solution is heated to about 50° C., the pH adjusted with 0.5N NaOH to about 6 and controlled by means of a pH meter or pH indicator paper and in a given case maintained at 6 by the addition of 0.5N NaOH. After about 5 hours it was filtered off from the precipitate and washed with a large amount of $H_2O$ and ethanol. The mostly yellow solids were dried in a high vacuum at 80° C. The frequently still orange filtrate is stirred for another 20 hours, whereby considerable amount of precipitate is formed. After renewed filtration the process repeated in part one more time. The complex compounds produced are entered in Table 1. The melting point of all platinum complexes set forth in Table 1 is above 250° C.

In the event it is not otherwise stated in Table 1 in the complexes in each case it is the DL-form (racemate).

The complexes which are set forth in Table 1 have a light yellow color.

TABLE 1

| Example No. | Group $-CH_2-B$ | Characteristic IR-Vibration Bands in $cm^{-1}$ (KBr) | | | |
| --- | --- | --- | --- | --- | --- |
| | | $\nu N-H$ | $\delta N-H$ | $\nu Pt-N$ | $\nu Pt-Cl$ |
| 1 (D-Form) | $-CH_2C_6H_5$ | 3275 s, 3190 s, 3120 m | 1567 s | 587 m | 302 m |
| 2 (L-Form) | $-CH_2C_6H_5$ | 3275 s, 3190 , 3120 m | 1567 | 587 m | 302 m |
| 3 | $-CH_2C_6H_5$ | 3280 vs, 3200 s, 3110 w | 1565 s | 555 w | 305 m, sh, 300 m |
| 4 | $-CH_2-C_6H_4-Cl$ (para) | 3265 vs, 3195 s, 3110 m | 1565 s | 568 | 310 m, sh, 300 m |
| 5 | $-CH_2-C_6H_3-Cl_2$ (2,3) | 3270 vs, 3195, 3110 m | 1565 s | 570 | 325 m, sh, 300 m, br |
| 6 | $-CH_2-C_6H_4-CF_3$ | 3265 s, 3195 s, 3110 s | 1565 s | 560 | 300 m, br |
| 7 | $-CH_2-C_6H_4-OCH_3$ | 3270 vs, 3200 s, 3120 m | 1565 m | 580 m | 300 m, br |
| 8 | $-CH_2-C_6H_4-OH$ | 3265 bs, 3200 s, 3110 m, sh | 1565 s | 580 | 305 m, br |
| 9 | $-CH_2-C_6H_3(OH)_2$ | 3280 vs, 3220 vs, 3140 s | 1575 s | | |
| 10 | $-CH_2-C_6H_3-O-CH_2-O$ | 3260 s, 3190 s, 3105 s | 1560 m, br | 520 w | 320 w, sh, 300 w |

TABLE 1-continued

| Example No. | Group —CH$_2$—B | Characteristic IR-Vibration Bands in cm$^{-1}$ (KBr) | | | |
| --- | --- | --- | --- | --- | --- |
| | | $\nu$N—H | $\delta$N—H | $\nu$Pt—N | $\nu$Pt—Cl |
| 11 | 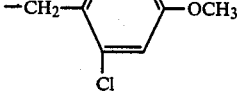 | 3280 vs, 3200 vs, 3120 vs, br | 1570 | | |
| 12 | 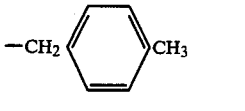 | 3275 s, 3195 s, 3115 w | 1567 s | 580 w | 300 m |
| 13 | 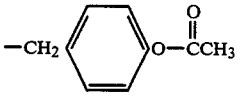 | 3265 vs, 3195 s, 3110 w | 1565 s | 570 w | 310 m |
| 14 | 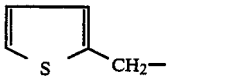 | 3270 vs, 3220 vs 3110 m | 1570 s | 325 m, 300 m | |
| 15 | 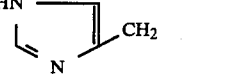 | 3200 vs, br, 3130 vs, br | 1585 s, br | 615 m | 325 m, sh, 310 m, br |
| 16 (L-Form) | 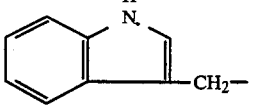 | 3410 s, br, 3350 s, sh br, 3260 vs, 3190 vs, 3110 | 1585 s, 1575 s, 1565 s | | |

$\nu$ = Stretching vibration S = strong, vs = very strong, m = moderately strong, sh = should, br = broad, $\delta$ = Deformation vibration, and w = weak

EXAMPLES 17-25

General Procedure Instructions

There were produced hereafter the platinum (II) complexes set forth in Table 2 of the following formula:

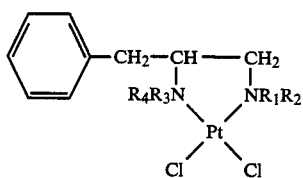

The complexes were obtained as light yellow, finely crystalline powders which were very lightly charged electrostatically. For example they are insoluble in H$_2$O, ether, ethyl acetate and similar agents, while the slight solubility in CHCl$_3$, CHCl$_2$, acetone, methanol, and ethanol increases with the number of the alkyl substituents on the nitrogen.

The complexes have good solubility in dimethyl formamide and dimethyl sulfoxide.

The complexes of Examples 17, 20, 21, 23, 24, 25, and 26 were produced as follows:

1 mole (415 mg) of potassium tetrachloroplatinate (II) were dissolved in 5 ml of water. There were added under stirring at room temperature dropwise a neutralized solution (pH 6-7) of 1 mmole of ligand (diamine or diamine dihydrochloride) in 5-10 ml of water. The solution was heated to about 50° C. and the pH was controlled continuously. In case it is necessary it was adjusted to pH 6 with 1N HCl or 1N NaOH.

After 10-30 minutes there begins to fall out a light yellow precipitate. After 4-5 hours stirring the solids formed up to them is filtered off, washed with a lot of water and a little (0.5 ml) ethanol. The yellow solids are dried in a high vacuum at 80° C. The still orange colored precipitate is stirred further at room temperature, whereby frequently only small amounts of further product accumulates. The complexes according to Examples 17, 20, 23, 24, and 25 melt above 250° C. The platinum complex according to Example 21 decompose at 190° C., the platinum complex according to claim 26 melts at 175° C.

The complexes of Examples 18, 19, 22, 27, and 28 are produced as follows:

1 mmole (415 mg) of K$_2$PtCl$_4$ were dissolved in 5 ml of water and under stirring dropped into a solution of 1 mole of ligand-diamine in 6 ml of dimethyl formamide. Should some ligand precipitate, more dimethyl formamide is added (about 5-10 ml). After addition of 1 ml of dimethyl sulfoxide the color changes within 10 minutes from orange to yellow. The mixture was concentrated at room temperature in a high vacuum and the oily residue treated with about 50 ml of water. The yellow complexes immediately precipitated and after long stirring at room temperature (about 1 day) became crystalline, the solids were filtered off with suction, washed with a lot of water and a little ethanol and dried in a high vacuum at 80° C. the complexes according to Examples 18 and 19 melt above 250° C. The complex according to Example 22 decomposes at 210° C. The complexes according to Examples 27 and 28 melt at 125 respectively 110° C.

(b) (S)-2-Amino-1-N,N-Dimethylamino-3-Phenylpropane

The production of 12.5 mmoles (3.4 grams) of (L)-

TABLE 2

| Ex. No. | $R_3$ | $R_4$ | $R_1$ | $R_2$ | \multicolumn{8}{c}{Characteristic IR—Vibration Bands in cm$^{-1}$ (KBr)} |
|---|---|---|---|---|---|---|---|---|---|---|---|---|
| | | | | | $\nu$N—H | | $\nu$C—H | $\delta$N—H | $\nu$C=C | $\delta$C—H | $\nu$Pt—N | $\nu$Pt—Cl |
| 17 | H | H | CH$_3$ | H | 3290 m<br>3180 s<br>3130 vs | 3070 m<br>3040 m | 2940 w | 1580 m | 1610 s<br>1500 s | 750 s<br>700 s | 580 w<br>465 w | 310 m |
| 18 | CH$_3$ | H | H | H | 3280 w<br>3200 m<br>3120 vs | 3040 w | 2960 w | 1580 m | 1605 w<br>1500 m | 745 s<br>730 s<br>695 s | 580 w<br>545 w<br>450 w | 310 m |
| 19 | CH$_3$ | H | CH$_3$ | H | 3120 vs | 3040 w | 2950 w<br>2870 vw | 1585 vw | 1605 w<br>1500 m | 745 s<br>700 s | 565 w<br>450 vw | 310 m |
| 20 | H | H | CH$_3$ | CH$_3$ | 3210 vs<br>3180 vs<br>3120 s | 3020 w | 2940 m<br>2870 vw | 1585 m | 1605 w<br>1500 s | 755 s<br>705 s | 585 m<br>545 m<br>460 m | 310 s |
| 21 | CH$_3$ | CH$_3$ | H | H | 3120 vs | 3030 m | 2940 m<br>2860 w | 1585 w | 1605 m<br>1500 s | 740 s<br>700 s | 580 m<br>450 m | 310 s |
| 22 | CH$_3$ | CH$_3$ | CH$_3$ | CH$_3$ | — | 3030 w<br>3000 m | 2940 s<br>2850 m | | 1605 w<br>1500 m | 740 vs<br>700 s | 580 w<br>435 w | 315 s |
| 23 | H | H | CH(CH$_3$)$_2$ | H | 3180 s<br>3120 vs | 3040 w | 2980 s | 1585 w | 1605 w<br>1500 m | 750 s<br>700 s | 580 s<br>465 s | 315 s |
| 24 | CH(CH$_3$)$_2$ | H | H | H | 3280 m<br>3200 vs | 3040 w | 2980 w | 1580 s | 1605 w<br>1500 m | 750 s<br>700 s | 585 w<br>460 w | 315 s |
| 25 | CH(CH$_3$)$_2$ | H | CH(CH$_3$)$_2$ | H | 3275 m<br>3190 s<br>3130 vs | 3040 s | 2980 vs | 1580 s | 1610 w<br>1500 s | 750 s<br>700 vs | 580 m<br>460 m | 315 s |
| 26 | CH$_3$ | H | CH—CH$_3$<br>\|<br>C$_6$H$_5$ | H | 3150 s | 3060 m<br>3030 m | 2980 w<br>2930 w | 1580 w | 1605 w<br>1500 s | 750 s<br>740 s<br>700 vs | 585 vw<br>520 w | 310 m |
| 27 | CH—CH$_3$<br>\|<br>C$_6$H$_5$ | H | H | H | 3230 s | 3080 m<br>3040 s | 2990 m<br>2930 w | 1590 w | 1610 w<br>1500 m | 750 s<br>700 vs | 595 vw<br>440 m | 330 m |
| 28 | CH$_2$C$_6$H$_5$ | H | H | H | 3230 s<br>3190 s | 3040 s<br>3070 s | 2920 m | 1590 w | 1610 m<br>1500 m | 750 s<br>700 vs | 575 vw<br>440 m | 320 m |

Production of the Starting Amines For Examples 17–28

(a) (S)-2-Amino-1-N-Methylamine-3-Phenyl-propane

Under ice cooling there were added in small portions 10 mmoles (178 grams) of (L)-phenylalanine methylamide to a stirred suspension of 30 mmoles (1.14 grams) of LiAlH$_4$ in about 50 ml of dry tetrahydrofuran. The mixture was heated for 24 hours at reflux. In order to hydrolyze excess LiAlH$_4$ there were added dropwise after cooling to 0° C. 120 mmoles (2.16 ml) of water. The mixture was filtered over a suction filter and the filtrate concentrated. The residue was extracted overnight with 150 ml of tetrahydrofuran in a Soxhlet apparatus. The extract was combined with the filtrate and the solvent distilled off in a vacuum. The lightly yellow crude product was distilled in a high vacuum ($10^{-4}$ Torr) at 75° C. air bath temperature, M.P. of the dihydrochloride 89° C.

The (L)-phenylalanine methylamide employed here was obtained as follows:

50 mmoles (8.96 grams) of (L)-phenylalanine methyl ester were dissolved in 75 ml of absolute methanol and cooled in an ice-salt bath to −10° C. Then the solution was saturated with dry methylamine (boiling point −7° C.) and stirred overnight. The cooling and introduction were repeated twice. The solvent was distilled off in a vacuum and the oily product obtained was recrystallized with a mixture of ethyl acetate-ether (1:1). When it was allowed to stand at −20° C. a white solid crystallized out, M.P. 57° C.

phenylalanine dimethylamide hydrobromide (production is given further below) and 37.5 mmoles (1.42 grams) of LiAlH$_4$ was carried out analogous to (a). High vacuum distillation at 100° C./$10^{-4}$ Torr (air bath temperature). The compound obtained is colorless oil.

N-Benzyloxycarbonyl-(L)-Phenylalanine 100 mmoles (16.51 grams) of (L)-phenylalanine were dissolved in 50 ml of 2N NaOH, cooled in an ice bath and treated dropwise with 106 mmoles (15.04 ml) of benzyl chloroformate. Stirring at room temperature was carried out for 30 minutes. If the product precipitates out already, sufficient water is added thereto until a clear solution is attained. 4N Hydrochloric acid is dropped in until acid reaction (pH4) and shaken three times with ethyl acetate. The organic phases were dried over sodium sulfate and freed from solvent in a vacuum. There was obtained a colorless, oily product. It was dissolved in 200 ml of chloroform, precipitated in the cold by addition of 400 ml of petroleum ether and filtered off with suction in a large suction filter. Colorless crystals.

Benzyloxycarbonyl-(L)-Phenylalanine Dimethylamide 20 mmoles (5.99 grams) of N-benzyloxycarbonyl-(L)-phenylalanine and 24 mmoles (2.76 grams) of N-hydroxysuccinimide are dissolved in 30 ml of chloroform and treated under ice cooling and stirring with 22 mmoles (4.34 grams) of dicyclohexylcarbodiimide dissolved in about 10 ml of chloroform. After 10 minutes stirring the mixture was cooled in an ice-salt bath to −10° C. and 20 mmoles (0.90 grams) of condensed, dry dimethylamine (boiling point +7° C.) added. Stirring was carried out for 24 hours, whereby the cooling bath was allowed to slowly melt. The precipitate formed was filtered off and the filtrate washed successively with each 20 ml 2N hydrochloric acid, saturated NaHCO$_3$ solution and water. After drying over sodium sulfate and drawing off the solvent in a vacuum there was obtained an oily product. It was distilled at 240° C. air bath temperature in a high vacuum (10$^{-4}$ Torr). Colorless, very viscous oil.

(L)-Phenylalanine Dimethylamide Hydrobromide 13 mmoles (4.28 grams) of benzyloxycarbonyl-(L)-phenylalanine dimethylamide is covered with 10 ml of ice cold saturated HBr-glacial acetic acid solution (40%) and stirred for 60 minutes at room temperature. The reaction mixture was concentrated in a vacuum. The colorless, oily product was treated with about 150 ml of ether and allowed to stand for 15 hours at −20° C. There formed a white crystalline solid. It was filtered off with suction, dried and without further purification used for the subsequent reduction.

(c) (S)-2-Amino-1-N-Isopropylamino-3-Phenyl-Propane

The production from 20 mmoles (5.74 grams) of (L)-phenylalanine isopropylamide hydrobromide (production see below) and 60 mmoles (2.28 grams) of LiAlH$_4$ was carried out analogous to (a). High vacuum distillation at 145° C./10$^{-4}$ Torr (air bath temperature). The amine is a colorless oil.

N-Benzyloxycarbonyl-(L)-Phenylalanine Isopropylamide 20 mmoles (5.99 grams) of N-benzyloxycarbonyl-(L)-phenylalanine and 24 mmoles (2.76 grams) of N-hydroxysuccinimide were dissolved in 30 ml of chloroform and treated under ice cooling and stirring with 22 mmoles (4.54 grams) of dicyclohexylcarbodiimide dissolved in about 10 ml of chloroform. After 10 minutes stirring at room temperature there were added 20 mmoles (1.71 ml) of isopropylamine. After 24 hours the precipitate formed was filtered off and the filtrate washed successively with 20 ml of dilute hydrochloric acid, saturated NaHCO$_3$ solution and water. The waxy residue obtained after drying over sodium sulfate and distilling off the solvent was recrystallized with ethyl acetate/petroleum ether. Colorless, crystalline material.

(L)-Phenylalanine-Isopropylamide Hydrobromide 20 mmoles (6.81 grams) of N-benzyloxycarbonyl-(L)-phenylalanine-isopropylamide were covered with 15 ml of ice cold saturated HBr solution (about 40%) and stirred for 60 minutes at room temperature. The reaction mixture was concentrated in a vacuum. The colorless, oily product was treated with about 150 ml of ether and allowed to stand for 15 hours at −20° C. There formed a very hygroscopic, white crystalline solid. It was filtered off by suction over a suction filter, dried and without further purification used for subsequent reduction (colorless crystal).

(d) (S)-2-N-Methylamino-1-(N-(S)-1-Phenylethylamino)-3-Phenylpropane

The preparation was carried out from 18.2 mmoles (7.30 grams) of N-benzyloxycarbonyl-(L)-phenylalanine-(S)-1-phenylethylamide (production see below) and 164 mmoles (6.22 grams) of LiAlH$_4$ analogous to (a). Hydrolysis was carried out with 656 mmoles (11.80) of water under ice cooling. In a high vacuum there first distilled off the benzyl alcohol formed (about 100° C.). The diamine boiled at about 150° C./10$^{-4}$ Torr (air bath temperature), colorless oil.

N-Benzyloxycarbonyl-(L)-Phenylalanine-(S)-1-Phenylethylamide

The production was carried out analogous to (c) from 20 mmoles (5.99 grams) of N-benzyloxycarbonyl-(L)-phenylalanine, 24 mmoles (2.76 grams) of N-hydroxysuccinimide, 22 mmoles (4.54 grams) of dicyclohexylcarbodiimide and 20 mmoles (2.53 grams) of (S)-1-phenylethylamine. Colorless solid, M.P. 99° C.

(3) 1-Amino-(S)-2-N-Methylamino-3-Phenylpropane

There was added 10 mmoles (2.36 grams) of N-ethyloxycarbonyl-(L)-phenylalanineamide (produced from (L)-phenylalanineamide and ethyl chloroformate in the presence of Na$_2$CO$_3$ in an ice bath) in small portions to an ice cooled suspension of 90 mmoles (3.41 grams) of LiAlH$_4$ in 110 ml of tetrahydrofuran. The mixture was heated at reflux for 24 hours. Hydrolysis was carried out under ice ooling with 360 mmoles (6.50 ml) of water. Further working up was analogous to (a). The product was distilled in a high vacuum (10$^{-4}$ Torr) at 75° C. air bath temperature. Colorless liquid, M.P. of the hydrochloride 160° C.

(f) 1-Amino-(S)-2-N,N-Dimethylamino-3-Phenylpropane 20 mmoles (3.28 grams) of (L)-phenylalanineamide were dissolved with stirring in 100 mmoles (3.85 ml) of 98% formic acid and treated with 60 mmoles (4.47 ml) of 37% aqueous formaldehyde solution. The mixture was heated briefly, until carbon dioxide development occured (about 2 to 3 minutes), and then stirring continued without supplying heat. When the gas development subsided heating was carried out at reflux at 100° C. for a further 15 minutes. After cooling there were added 20 ml of 2N hydrochloric acid and the product freed from excess starting materials on the rotary evaporator. The yellow, oily residue was taken up in 7 ml of water and the amine set free by addition of 5 ml of 18N aqueous sodium hydroxide. The organic phase was separated off and the aqueous phase shaken twice with 10 ml of ethyl acetate. The combined organic phases were dried over potassium carbonate and freed from solvent. There were obtained 17.3 mmoles (3.32 grams) of N,N-dimethylamino-(L)-phenylalanineamide as a yellow colored oil. This was added in portions to an ice cooled suspension of 69 mmoles (2.62 grams) of LiAlH$_4$ in about 100 ml of tetrahydrofuran and heated at reflux for 24 hours. Hydrolysis was carried out under ice cooling with 276 mmoles (4.97 ml) of water. Further working up was analogous to (a). The product was distilled in a high vacuum (10$^{-4}$ Torr) at 90° C. air bath temperature (colorless oil).

(g) 1-Amino-(S)-2-N-Isopropylamino-3-Phenylpropane 20 mmoles (3.20 grams) of (L)-phenylalanineamide were dissolved in 125 ml of benzens, treated with 20 mmoles (1.47 ml) of acetone and a spatula tip of p-toluenesulfonic acid and heated at reflux for 12 hours in a Soxhlet apparatus which is filled with CaSO$_4$·½H$_2$O as drying agent. After drawing off the solvent in vacuum there was obtained a light sensitive viscous oil as the condensation product. This was added under ice cooling to a suspension of 100 moles (3.79 grams) of LiAlH$_4$ in 100 ml of tetrahydrofuran and heated overnight at reflux. The excess LiAlH$_4$ was hydrolyzed by slowly dropping in 400 mmoles (7.20 ml) of water (in an ice bath). The product was filtered over a suction filter and the filtrate concentrated. The residue was extracted overnight with 150 ml of tetrahydrofuran in a Soxhlet apparatus. The extract was combined with the filtrate and the solvent distilled off in a vacuum. The yellowish oil obtained was distilled in a high vacuum at 80° C. air bath temperature (colorless liquid).

In the preceding directions if there is employed 20 mmoles (2.33 ml) of acetophenone or 20 mmoles (2.02 ml) of benzaldehyde in place of 20 mmoles (1.47 ml) of acetone then there are formed the compounds 1-amino-(S)-2-(N-(R,S)-1-phenylethylamine)-3-phenylpropane (distillation at 150° C. air bath temperature in a high vacuum; colorless liquid) or 1-amino-(S)-2-N-benzylamino-3-phenyl-propane (distillation at 145° C. air bath temperature in a high vacuum; colorless liquid).

(h) (S)-1,2-Bis(N-Methylamino)-3-Phenylpropane 225 mmoles (9.00 grams) of NaOH were dissolved in 45 ml of water, cooled in an ice bath and treated with 49 mmoles (7.35 grams) of (S)-1,2-diamino-3-phenylpropane dissolved in about 45 ml of benzene. Within 30 minutes with stirring there was dropped in a solution of 108 mmoles (10.3 ml) of ethyl chloroformate in 45 ml of benzene and the mixture allowed to stir for 3 hours at room temperature. The organic phase was separated off and the aqueous solution shaken twice with 20 ml of benzene. The combined phases were dried over sodium sulfate and freed from solvent. There were obtained 40.33 mmoles (11.87 grams) of colorless, crystalline solid [(S)-1,2-bis(N-ethyloxycarbonylamino)-3-phenyl-propane]. This was added in small portions to an ice cooled suspension of 370 mmoles (14.0 grams) of LiAlH$_4$ in 300 ml of tetrahydrofuran. After heating for 24 hours under reflux by ice cooling the product was carefully hydrolyzed with 1.5 moles (27 ml) of water. The hydrolysis products were filtered off and the filtrate concentrated. The residue was extracted for 12 hours with 150 ml of tetrahydrofuran in a Soxhlet apparatus. The extract was combined with the filtrate and the solvent distilled off in a vacuum. The light brownish liquid was distilled in a high vacuum at 85° C. Colorless liquid.

(i) (S)-1,2-Bis(N-Isopropylamino)-3-Phenylpropane 21.2 mmoles (3.18 grams) of (S)-1,2-diamino-3-phenylpropane were dissolved in 12 ml of benzene, treated with 42.4 mmoles (3.11 ml) of acetone and a spatula tip of p-toluenesulfonic acid. The mixture was heated for 12 hours under reflux in a Soxhlet apparatus which is filled with calcined calcium sulfate as drying agent. After drawing off the solvent in a vacuum there was obtained a light yellowish oil. It was dissolved in 50 ml of methanol, cooled in an ice-salt bath to −10° C. and treated with 80.0 mmoles (3.03 grams) of NaBH$_4$. It was allowed to come to room temperature under stirring and heated for a further 12 hours under reflux. After cooling the solvent was distilled in a vacuum and hydrolyzed with 30 ml of water. It was shaken with 150 ml of ether and the organic phase washed twice with 30 ml of water each time. After drying over sodium sulfate the ether was drawn off and the brownish oil obtained was distilled in a high vacuum at 100° C. air bath temperature. Colorless oil.

Production of the Diamine Dihydrochloride

For purification purposes the diamines were convered into their dihydrochlorides. The best results were obtained by introducing dry hydrogen chloride gas into well cooled etheric solution of the diamine: about 2 grams of diamine were dissolved in 5 ml of ethanol, treated with 50 ml of ether and cooled in the ice-salt bath to −15° C. Then a slow stream of dry HCl gas was led in until separation of a white, crystalline precipitate. With too great an excess of HCl the precipitate accumulates as an oil. The dihydrochlorides which for the most part are moisture sensitive are filtered off with suction and dried in a high vacuum.

Conversion of the Dihydrochloride into the Diamine

About 10 mmoles of dihydrochloride were boiled under reflux for 30 minutes with 20 ml of ether and 10 ml of triethylamine. The precipitated triethylammonium chloride is filtered off with suction and the filtrate freed from excess solvent and triethylamine in a vacuum. The oils obtained were distilled in a high vacuum.

The following Table 3 with Examples 29 to 36 is directed once again to platinum complexes of the formula

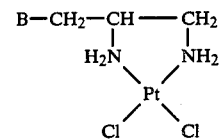

The production of the compounds is carried out according to the procedure which is given for Examples 1 to 16.

| Example No. | Group —CH$_2$—B | Characteristic IR-Vibration Band in cm$^{-1}$ (KBr) | | | |
|---|---|---|---|---|---|
| | | $\nu$N—H | $\delta$N—H | $\nu$Pt—N | $\nu$Pt—Cl |
| 29 | —CH$_2$—C$_6$H$_4$—Cl (ortho) | 3280 cm$^{-1}$, vs<br>3200 cm$^{-1}$, s<br>3120 cm$^{-1}$, m | 1560 cm$^{-1}$, s | 570 cm$^{-1}$, w | 305 cm$^{-1}$, m, br |
| 30 | —CH$_2$—C$_6$H$_4$—Cl (ortho) | 3270 cm$^{-1}$, vs<br>3190 cm$^{-1}$, s<br>3120 cm$^{-1}$, m | 1560 cm$^{-1}$, s, b | 560 cm$^{-1}$, w | 300 cm$^{-1}$, m, br |
| 31 | —CH$_2$—C$_6$H$_3$Cl$_2$ | 3270 cm$^{-1}$, s<br>3200 cm$^{-1}$, s<br>3120 cm$^{-1}$, m | 1560 cm$^{-1}$, s | 570 cm$^{-1}$, w | 300 cm$^{-1}$, m, br |

-continued

| Example No. | Group —CH₂—B | Characteristic IR-Vibration Band in cm⁻¹ (KBr) | | | |
|---|---|---|---|---|---|
| | | $\nu$N—H | $\delta$N—H | $\nu$Pt—N | $\nu$Pt—Cl |
| 32 | —CH₂—C₆H₄—Br (ortho) | 2260 cm⁻¹, s<br>2190 cm⁻¹, vs<br>3120 cm⁻¹, s | 1570 cm⁻¹, s | 590 cm⁻¹, m<br>440 cm⁻¹, m | 310 cm⁻¹, m, br |
| 33 | —CH₂—C₆H₄—Br (para) | 3270 cm⁻¹, s<br>3200 cm⁻¹, s<br>3120 cm⁻¹, m | 1560 cm⁻¹ | 590 cm⁻¹, s<br>470 cm⁻¹, m | 310 cm⁻¹, m, br |
| 34 | —CH₂—C₆H₄—F | 3270 cm⁻¹, vs<br>3190 cm⁻¹, s<br>3120 cm⁻¹, m | 1565 cm⁻¹ | 580 cm⁻¹, m<br>490 cm⁻¹, , | 300 cm⁻¹, m, br |
| 35 | —CH₂—C₆H₄—NO₂ | 3260 cm⁻¹, s<br>3190 cm⁻¹, vs<br>3110 cm⁻¹, m | 1560 cm⁻¹, s | 590 cm⁻¹, w | 310 cm⁻¹, m, br |
| 36 | 2,6-dichloro-4-hydroxyphenyl | 3270 cm⁻¹, s<br>3200 cm⁻¹, vs<br>3120 cm⁻¹, s | 1580 cm⁻¹, s | 560 cm⁻¹, m | 310 cm⁻¹, m |

EXAMPLE 37

Exchange of the Anion X for Other Anions 1 mmole (416.2 mg) of the dichlorocomplex (DL-form) of the formula

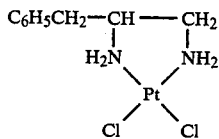

was suspended in 5 to 10 ml of H₂O and treated with 2 mmoles (339.7 mg) of AgNO₃ dissolved in 5 ml of H₂O. The reaction mixture was stirred in the dark. Already after a few hours in the gradual change of the initial yellow color of the dichlorocomplex to the white-gray color of the silver chloride formed there is recognized progress of the reaction. After about two to seven days the silver chloride is filtered off, the pH brought to 4 to 5 by addition of 0.5 molar ammonia solution and the clear filtrate treated with 1 mmole of the acids 1,1-cyclobutanedicarboxylic acid, malonic acid, hydroxymalonic acid, benzenesulfonic acid, tartaric acid, α-chloroacetic acid, aspartic acid, phthalic acid as well as 4-carboxyphthalic acid or the salts sodium oxalate and sodium isocitrate in solid form. In most cases already after a few hours the separation of the yellow or white complexes begins, which is stirred for a further 20 hours. Then it was filtered off, washed with ice cold water and dried in a high vacuum at 80° C.

In this manner there are obtained for example complexes of the above-stated formula, in which the two chlorine anions are replaced by the divalent anions of the following acids: oxalic acid (white powder, M.P. >250° C.); 1,1-cyclobutanedicarboxylic acid (white powder, M.P. 250° C.); 4-carboxy-phthalic acid (white powder, M.P. 222° C., decomposition); phthalic acid (white powder, M.P. 185° C., decomposition); isocitric acid (light yellow powder, M.P. 226° C., decomposition); tartaric acid (white powder, M.P. 215° C., decomposition); aspartic acid (white powder, M.P. 130° C., decomposition).

Because of the good water solubility of the dibenzenesulfonate complexes, the α-chloroacetate-nitrate complexes and the dinitrate complexes in these cases there was concentration in high vacuum until formation of a viscous residue, which was treated with ether. After a short stirring these complexes likewise were obtained as white solids, which were filtered off and dried in a high vacuum.

The benzenesulfonate complex (X=C₆H₅SO₃) is a white powder which melts at 170° C. with decomposition. The α-chloroacetate-nitrate complex (one X=NO₃, the other X=CH₂Cl—CO₂) is a beige powder which melts at 148° C. with decomposition.

The dinitrate complex (with 2 moles of H₂O) is a yellow powder, M.P. 250° C.

There were obtained from the dichloro-complex (DL-form) of the formula

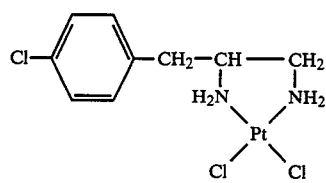

in analogous manner for example complexes where the two anions X have the following meaning:

The two anions X form together the malonic aion ($^\ominus O_2C-CH_2-CO_2^\ominus$).

The complex is a colorless solid. Decomposition point 307° C.

The two anions X form together the hydroxymalonic acid anion ($^\ominus O_2C-CH(OH)-CO_2^\ominus$).

The complex is a colorless, water soluble solid; decomposition point 270° C.

Complex with the tetra anion of 1,2,3,4,5-benzenepentacarboxylic acid (it is a matter of a bis complex whereby 1 mole of the anionic compound is bound with 1 moles of the platinum component):

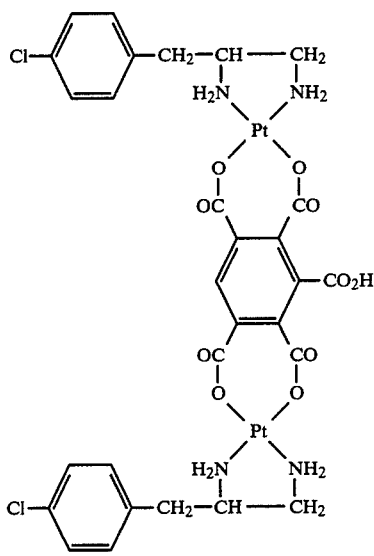

The complex is a white powder which melts above 160° C. with decomposition.

Each anion X is the anion of the aminoacid ornithine (L-form, whose two amino groups are acetylated).

The complex is a white powder; Melting Point 115° C. (under decomposition).

EXAMPLES OF GALENICAL PREPARATIONS

Coated Tablets 200 grams of the compound of Example 3, 300 grams of lactose D 10, 130 grams of corn starch and 10 grams of magnesium stearate were passed through a sieve having a mesh width of 0.8 mm and homogenized.

This composition was pressed in known manner to curved tablets weight 100 mg.

For the production of coated tablets these nuclei with the help of a spraying apparatus in known manner were provided with stomach or small intestine soluble coating which can consist of a suitable polymeric film former, such as for example, acrylate esters or methacrylate ester and suitable adjuvants such as wetting agents, plasticizers, dyestuffs, lubricants, etc. The nuclei also can be processed in customary manner to dragees. One film tablet or one dragee contains 20 mg of active material.

Lyophilizate:

There were dissolved with stirring in 800 ml of water for injection purposes 50 grams of mannitol and 5 grams of (D,L-dibenzenesulfonate-(1-benzylethylenediamine)-platinum II (compound according to Example 37) and the volume filled up to 1 liter with water for injection purposes.

This solution was sterile filtered under aseptic conditions over a membrane filter having a pore size of 0.22 μm and filled to 10 ml in 15 ml injection flasks of hydrolytic class I. The flasks were provided with freeze dry stoppers and lyophilized in a suitable apparatus. After the drying gassing was carried out with dried nitrogen and the flasks closed in the apparatus. The stoppers were secured by an edge cap.

For the intravenous use the lyophilizate was reconstituted in 10 ml of injection water.

1 ml of solution contains 5 mg of active material.

The entire disclosure of German priority application No. P3506468.4 is hereby incorporated by reference.

What is claimed is:

1. (1-benzyl-ethylenediamine)-platin(II)-complexes of the general formula:

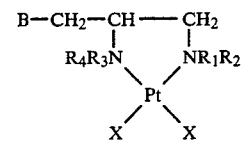

wherein the radicals $R_1$, $R_2$, $R_3$, and $R_4$ are the same or different and are hydrogen, a $C_1$-$C_6$-alkyl group, a benzyl group, or a phenylethyl group, and B is a thienyl radical, an indolyl radical, an imidazolyl radical, or a phenyl radical substituted by the radicals $R_5$, $R_6$, and $R^7$ which are the same or different and are hydrogen, halogen, trihalomethyl, $C_1$-$C_6$-alkyl, hydroxy, $C_1$-$C_6$-alkoxy, $C_1$-$C_6$-alkanoyloxy, nitro and two of these groups can be the methylenedioxy group and X is the equivalent of a physiologically compatible anion, as well as optionally their salts with physiologically compatible cations and anions.

2. A compound according to claim 1 wherein B is a phenyl group which contains one or two halogen atoms.

3. A compound according to claim 2 wherein the halogen atom or atoms are chlorine atoms.

4. A compound according to claim 1 wherein B is a phenyl radical substituted by $R_5$, $R_6$ and $R_7$ and wherein at least one of $R_5$, $R_6$ and $R_7$ is halogen.

5. A compound according to claim 1 wherein B is a thienyl radical, an indolyl radical or an imidazolyl radical.

6. A compound according to claim 1 wherein $R_1$, $R_2$, $R_3$ and $R_4$ are all hydrogen.

7. A compound according to claim 1 wherein at least one of $R_1$, $R_2$, $R_3$ and $R_4$ is not hydrogen.

* * * * *